(12) United States Patent
Mohammed et al.

(10) Patent No.: US 8,021,888 B2
(45) Date of Patent: Sep. 20, 2011

(54) RAPID COMPARATIVE GENOMIC HYBRIDIZATION USING ACOUSTIC SURFACE WAVES

(75) Inventors: Mansoor S. Mohammed, Mission Viejo, CA (US); Natasa Dzidic, San Clemente, CA (US); Christopher McCaskill, Lake Elsinore, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 495 days.

(21) Appl. No.: 11/883,150

(22) PCT Filed: Jan. 26, 2006

(86) PCT No.: PCT/US2006/002780
§ 371 (c)(1),
(2), (4) Date: Oct. 17, 2008

(87) PCT Pub. No.: WO2006/081353
PCT Pub. Date: Aug. 3, 2006

(65) Prior Publication Data
US 2009/0069191 A1 Mar. 12, 2009

Related U.S. Application Data

(60) Provisional application No. 60/648,377, filed on Jan. 27, 2005.

(51) Int. Cl.
 G01N 33/00 (2006.01)
 G01N 33/53 (2006.01)
 C07H 21/04 (2006.01)
 C12Q 1/68 (2006.01)
 C12M 1/34 (2006.01)

(52) U.S. Cl. ........... 436/94; 436/800; 435/6; 435/287.2; 536/23.1; 536/24.33

(58) Field of Classification Search .................. None
See application file for complete search history.

(56) References Cited

U.S. PATENT DOCUMENTS

| | | | |
|---|---|---|---|
| 4,788,466 A * | 11/1988 | Paul et al. | 310/323.06 |
| 5,143,854 A | 9/1992 | Pirrung et al. | |
| 5,374,521 A * | 12/1994 | Kipling et al. | 435/6 |
| 5,434,049 A | 7/1995 | Okano et al. | |
| 5,539,517 A | 7/1996 | Cabib et al. | |
| 5,556,752 A | 9/1996 | Lockhart et al. | |
| 5,595,908 A * | 1/1997 | Fawcett et al. | 435/287.2 |
| 5,632,957 A | 5/1997 | Heller et al. | |
| 5,635,351 A | 6/1997 | Feuerstein et al. | |
| 5,665,549 A | 9/1997 | Pinkel et al. | |
| 5,700,637 A | 12/1997 | Southern | |
| 5,721,098 A | 2/1998 | Pinkel et al. | |
| 5,744,305 A | 4/1998 | Fodor et al. | |
| 5,770,456 A | 6/1998 | Holmes | |
| 5,790,727 A | 8/1998 | Dhadwal et al. | |
| 5,800,992 A | 9/1998 | Fodor et al. | |
| 5,807,522 A | 9/1998 | Brown et al. | |
| 5,830,645 A | 11/1998 | Pinkel et al. | |
| 5,846,708 A | 12/1998 | Hollis et al. | |
| 5,856,097 A | 1/1999 | Pinkel et al. | |
| 5,856,174 A | 1/1999 | Lipshutz et al. | |
| 5,880,473 A | 3/1999 | Ginestet | |
| 5,922,617 A | 7/1999 | Wang et al. | |
| 5,943,129 A | 8/1999 | Hoyt et al. | |
| 5,959,098 A | 9/1999 | Goldberg et al. | |
| 5,965,362 A | 10/1999 | Pinkel et al. | |
| 5,965,452 A | 10/1999 | Kovacs | |
| 5,976,790 A | 11/1999 | Pinkel et al. | |
| 6,013,440 A | 1/2000 | Lipshutz et al. | |
| 6,022,963 A | 2/2000 | McGall et al. | |
| 6,045,996 A | 4/2000 | Cronin et al. | |
| 6,048,695 A | 4/2000 | Bradley et al. | |
| 6,049,380 A | 4/2000 | Goodwin et al. | |
| 6,054,270 A | 4/2000 | Southern | |
| 6,054,279 A | 4/2000 | Nadeau et al. | |
| 6,055,325 A | 4/2000 | Garini et al. | |
| 6,066,459 A | 5/2000 | Garini et al. | |
| 6,140,044 A | 10/2000 | Besemer et al. | |
| 6,143,495 A | 11/2000 | Lizardi et al. | |
| 6,159,685 A | 12/2000 | Pinkel et al. | |
| 6,191,425 B1 | 2/2001 | Imai | |
| 6,197,501 B1 | 3/2001 | Cremer et al. | |
| 6,252,664 B1 | 6/2001 | Barberá-Guillem | |
| 6,258,606 B1 | 7/2001 | Kovacs | |
| 6,261,776 B1 | 7/2001 | Pirrung et al. | |

(Continued)

FOREIGN PATENT DOCUMENTS

WO    WO 93/18186    9/1993

(Continued)

OTHER PUBLICATIONS

Allawi, Hatim T. and Jr., SantaLucia, John, Thermodynamics and NMR of Internal G•T Mismatches in DNA, *Biochemistry* 36:10581-94, (1997).

(Continued)

*Primary Examiner* — Bradley L Sisson
(74) *Attorney, Agent, or Firm* — Foley & Lardner LLP

(57) ABSTRACT

Disclosed is a method for performing nucleic acid hybridization assays which involve the application of acoustic surface waves. The hybridization assays may be used for detecting and mapping chromosomal or genetic abnormalities associated with various diseases or associated with predisposition to various diseases. In a particular aspect, the present method relates to the use of rapid nucleic acid hybridization methods, such as comparative genomic hybridization (CGH), for comparing nucleic acid segments of one genome to corresponding nucleic acid segments in another genome(s).

12 Claims, No Drawings

U.S. PATENT DOCUMENTS

| | | | |
|---|---|---|---|
| 6,277,489 | B1 | 8/2001 | Abbott et al. |
| 6,277,628 | B1 | 8/2001 | Johann et al. |
| 6,294,331 | B1 | 9/2001 | Ried et al. |
| 6,335,167 | B1 | 1/2002 | Pinkel et al. |
| 6,562,565 | B1 | 5/2003 | Pinkel et al. |
| 2001/0007747 | A1 | 7/2001 | Bochkariov et al. |
| 2001/0008765 | A1 | 7/2001 | Shinoki et al. |
| 2001/0012537 | A1 | 8/2001 | Anderson et al. |
| 2001/0014448 | A1 | 8/2001 | Chappa et al. |
| 2001/0014449 | A1 | 8/2001 | Nerenberg et al. |
| 2001/0016322 | A1 | 8/2001 | Caren et al. |
| 2001/0018514 | A1 | 8/2001 | McGall et al. |
| 2001/0018642 | A1 | 8/2001 | Balaban et al. |
| 2001/0019827 | A1 | 9/2001 | Dawson et al. |
| 2001/0055529 | A1 | 12/2001 | Wixforth |
| 2003/0040005 | A1* | 2/2003 | Jensen et al. ............ 435/6 |
| 2004/0072208 | A1* | 4/2004 | Warthoe et al. ........... 435/6 |
| 2004/0197806 | A1* | 10/2004 | Yoshida et al. ........... 435/6 |
| 2004/0208792 | A1* | 10/2004 | Linton et al. ............ 422/99 |
| 2004/0209280 | A1* | 10/2004 | Sundararajan et al. ..... 435/6 |
| 2004/0253648 | A1* | 12/2004 | Fletterick et al. ........ 435/7.2 |

FOREIGN PATENT DOCUMENTS

| | | |
|---|---|---|
| WO | WO 96/17958 | 6/1996 |
| WO | WO 97/46313 | 12/1997 |
| WO | WO 99/09217 | 2/1999 |
| WO | WO 99/51773 | 10/1999 |
| WO | WO 99/60163 | 11/1999 |
| WO | WO 00/09650 | 4/2000 |
| WO | WO 00/26412 | 5/2000 |
| WO | WO 00/42222 | 7/2000 |
| WO | WO 00/47600 | 8/2000 |
| WO | WO 01/01144 | 1/2001 |
| WO | WO 01/46467 | 6/2001 |

OTHER PUBLICATIONS

Bowtell, David D.L., Options available—from start to finish—for obtaining expression data by microarray, *Nature Genetics* Supp. 21:25-32, 1999.

Daigo et al., Degenerate Oligonucleotide Primed-Polymerase chain Reaction-Based Array Comparative Genomic Hybridization for Extensive Amplicon Profiling of Breast Cancers—A New Approach for the Molecular Analysis of Paraffin-Embedded Cancer Tissue, *Am. J. Pathol.* 158:1623-1631, (2001).

Jain, K.K., Applications of biochip and microarray systems in pharmacogenomics, *Pharmacogenomics* 1:289-307, (2000).

Johnston, Mark, Gene chips: Array of hope for understanding gene regulation, *Curr. Biol.* 8:R171-R174, (1998).

Kallioniemi et al., Comparative Genomic Hybridization for Molecular Cytogenetic Analysis of Solid Tumors, Science 258:818-821, (1992).

Kern, Suzanne and Hampton, Garret M., Direct Hybridization of Large-Insert Genomic Clones on High-Density Gridded cDNA Filter Arrays, *Biotechniques* 23:120-124, (1997).

Klinger et al., Rapid Detection of Chromosome Aneuploidies in Uncultured Amniocytes by Using Fluorescence In Situ Hybridization (FISH), *Am. J. Hum. Genet.* 51:52-65, (1992).

Mansfield et al., Nucleic acid detection using non-radioactive labelling methods, *Mol. Cell. Probes* 9:145-156, (1995).

Schummer et al., Inexpensive Handheld Device for the Construction of High-Density Nucleic Acid Arrays, *Biotechniques* 23:1087-1092, (1997).

Solinas-Toldo et al., Matrix-Based Comparative Genomic Hybridization: Biochips to Screen for Genomic Imbalances, *Genes, Chromosomes & Cancer* 20:399-407, (1997).

Theillet, Le typage genomique: de la cytogenetique moleculaire aux puces a ADN. *Bull. Cancer* 88:261-268, 2001 (An abstract in English is on front page of article).

Werner, Thomas, Cluster analysis and promoter modelling as bioinformatics tools for the identification of target genes from expression array data, *Pharmacogenomics* 2:25-36, (2001).

Toegl et al., Enhancing results of microarray hybridizations through microagitation. Journal of Biomolecular Techniques, 14:197-204, 2003.

Wixforth et al., Acoustic manipulation of small droplets. Anal. Bioanal. Chem., 379:982-991, 2004.

Vo-Dinh, Development of a DNA biochip: principle and applications. Sensors and Actuators B 51: 52-59, 1998.

Zhai Junhui, DNA based biosensors. Biotechnology Advances. 15(1): 43-58, 1997.

Supplementary European Search Report for EPO Patent Application No. 06 71 9586.

\* cited by examiner

RAPID COMPARATIVE GENOMIC HYBRIDIZATION USING ACOUSTIC SURFACE WAVES

FIELD

The present method relates to nucleic acid hybridization assays, such as assays used for detecting and mapping chromosomal or genetic abnormalities associated with various diseases or associated with predisposition to various diseases. In a particular aspect, the present method relates to improvements that shorten the assay time, thus, increasing the utility of such assays.

BACKGROUND

Nucleic acid hybridization assays are useful for detecting and comparing nucleic acids. Generally, hybridization assays include the following major steps: (1) immobilization of nucleic acids to a support to provide an immobilized probe; (2) pre-hybridization treatment to increase accessibility of the probe and to reduce nonspecific binding; (3) hybridization of a mixture of target nucleic acids to the probe; (4) post-hybridization washes to remove nucleic acid fragments not hybridized to the probe; and (5) detection of the target nucleic acid hybridized to the probe.

Comparative genomic hybridization ("CGH") is one useful type of nucleic acid hybridization assay. CGH was originally developed to detect and identify the location of a gain or loss of DNA sequences, such as deletions, duplications or amplifications commonly seen in tumors (Kallioniemi et al., Science 258:818-821, 1992). For example, genetic changes resulting in an abnormal number of one or more chromosomes (i.e., aneuploidy) have provided useful diagnostic indicators of human disease, specifically as cancer markers. Changes in chromosomal copy number are found in nearly all major human tumor types. For a review, see Mittelman et al., "Catalog of Chromosome Aberrations" in CANCER, Vol. 2 (Wiley-Liss, 1994).

In addition, CGH has been used to detect the presence of aneuploid cells as a marker for genetic chromosomal abnormalities. Various chromosomal abnormalities may occur in an estimated 0.5% of all live births. For example, Down's syndrome or trisomy 18 which has an incidence of about 1 in 800 live births, is commonly the subject of a variety of pre-natal screens or diagnostic techniques. Chromosomal aneuploidies involving chromosomes 13, 18, 21, X and Y account for up to 95% of all liveborn chromosomal aberrations resulting in birth defects (Whiteman et al., Am. J. Hum. Genet. 49:A127-129, 1991), and up to 67% of all chromosomal abnormalities, including balanced translocations (Klinger et al., Am. J. Hum. Genet. 51:52-65, 1992).

CGH is useful to discover and map the location of genomic sequences with variant copy number without prior knowledge of the sequences. Early CGH techniques employ a competitive in situ hybridization between test DNA and normal reference DNA, each labeled with a different color, and a metaphase chromosomal spread. Chromosomal regions in the test DNA, which are at increased or decreased copy number as compared to the normal reference DNA can be quickly identified by detecting regions where the ratio of signal from the two different colors is altered. For example, those genomic regions that have been decreased in copy number in the test cells will show relatively lower signal from the test DNA than the reference (compared to other regions of the genome (e.g., a deletion)); while regions that have been increased in copy number in the test cells will show relatively higher signal from the test DNA (e.g., a duplication). Where a decrease or an increase in copy number is limited to the loss or gain of one copy of a sequence, CGH resolution is usually about 5-10 Megabases (Mb).

In a typical array-based CGH, equivalent amounts of total genomic nucleic acid from cells of a test sample and a normal reference sample are labeled with two different colors of fluorescent dye and co-hybridized to an array of BACs, which contain the cloned nucleic acid fragments that collectively cover the cell's genome. The resulting co-hybridization produces a fluorescently labeled array, the coloration of which reflects the competitive hybridization of sequences in the test and reference genomic DNAs to the homologous sequences within the arrayed BACs. Theoretically, the copy number ratio of homologous sequences in the test and reference genomic nucleic acid samples should be directly proportional to the ratio of their respective colored fluorescent signal intensities at discrete BACs within the array. Array-based CGH is described in U.S. Pat. Nos. 5,830,645 and 6,562,565 for example, using target nucleic acids immobilized on a solid support in lieu of a metaphase chromosomal spread.

Typically, an array-based CGH assay takes more than one day to complete. In particular, the hybridization step is typically performed overnight to achieve suitable results.

SUMMARY

Disclosed is a method for performing a rapid hybridization assay. The method can be used to reduce the time to complete nucleic acid hybridization between nucleic acids in solution and nucleic acid immobilized to a solid support. The method applies acoustic surface waves during any of prehybridization to non-specific nucleic acid, hybridization to target nucleic acid or during any washing steps following hybridization. In one approach, nucleic acid hybridization to immobilized nucleic acid includes the following steps:

a) contacting a solid support comprising one or more immobilized nucleic acid probe molecules under hybridization conditions with a non-specific blocking nucleic acid wherein the one or more immobilized nucleic acid probe molecules are capable of hybridizing with a sequence complementary thereto;

b) contacting the solid support under hybridization conditions with a test sample containing nucleic acid target molecules;

c) applying acoustic surface waves to the hybridization of step a) or step b) or both; and d) determining whether the one or more nucleic acid probes of the solid support have hybridized to test sample nucleic acid target molecules.

The concentration of the non-specific nucleic acid can vary. In a preferred embodiment, the concentration of non-specific nucleic acid is at least about 1 mg/ml. The non-specific nucleic acid is preferably Cot-1 DNA.

In another approach, nucleic acid hybridization to immobilized nucleic acid includes the following steps:

a) contacting a solid support containing one or more immobilized nucleic acid probe molecules under hybridization conditions with a nucleic acid test sample containing one or more nucleic acid target molecules, the one or more immobilized nucleic acid probe molecules capable of hybridizing with a sequence complementary thereto;

b) applying acoustic surface waves to the hybridization of step a); and c) determining whether the one or more nucleic acid probes of the solid support has hybridized to test sample nucleic acid target molecules.

This method also may include a prehybridization step with non-specific nucleic acid such as described for the method further above. One or more washing steps may be applied after the prehybridization step or the hybridization step. One or more washing steps may include application of acoustic surface waves.

With the application of acoustic waves, the prehybridization step may be limited to less than about 7 hours, more preferably less than about 5 hours and even more preferably less than about 3 hours. The hybridization step to target nucleic acid may be less than about 3 hours, more preferably less than about 2 hours and even more preferably less than about 1 hours. The washing steps are performed for less than about 1 hour, more preferably less than about 30 minutes. In a preferred embodiment, the method is performed in less than about 9 hours, more preferably less than about 7 hours and even more preferably less than about 5 hours.

The method of hybridization to a test nucleic acid target molecule may further include one or more reference nucleic acid target molecules. The test and/or reference nucleic acid target molecules may be labeled with a detectable agent.

In some embodiments, the solid support may contain an array of immobilized nucleic acid probe molecules. In some embodiments, the immobilized nucleic acid probe molecules may include the sequence of a bacterial artificial chromosome.

DETAILED DESCRIPTION OF THE PREFERRED EMBODIMENTS

Described herein is a method for performing a rapid hybridization assay. In one aspect, provided herein is a rapid method for detecting a chromosomal abnormality in a test sample. The first step of this method typically includes contacting under hybridization conditions a test sample that includes multiple nucleic acids with a solid support that includes one or more nucleic acid segments each immobilized at discrete locations on the surface. Typically, an array of immobilized nucleic acid probes are used. Optionally, a reference sample that includes multiple nucleic acids may be mixed with the test nucleic acids before contacting the immobilized nucleic acid probes. The test and reference nucleic acid may include sequence from some or all of the genome of a cell.

The nucleic acids obtained from the test sample and reference sample both may be labeled with a detectable label which is linked via a linkage. To facilitate hybridization, acoustic surface waves are applied to the hybridization reaction. Following hybridization, washing with an appropriate stringency may be used to remove any non-hybridized or weakly hybridized nucleic acid. To facilitate washing, acoustic surface wave may be applied. The final step includes identifying or measuring sample or reference nucleic acids that have hybridized to nucleic acid probes of the support. In the case of an array, this step can be referred to as to "read" the array.

As used herein, "nucleic acid" refers to segments or portions of DNA, cDNA, and/or RNA. Nucleic acid may also be derived or obtained from an originally isolated nucleic acid sample from any source (e.g., isolated from, purified from, amplified from, cloned from, reverse transcribed from sample DNA or RNA). "Genomic nucleic acid" refers to some or all of the DNA from the nucleus of a cell. In some embodiments, genomic DNA may include sequence from all or a portion of a single gene or from multiple genes, sequence from one or more chromosomes, or sequence from all chromosomes of a cell. Genomic nucleic acid may be obtained from the nucleus of a cell, or recombinantly produced. Genomic DNA may be transcribed from DNA or RNA isolated directly from a cell nucleus. PCR amplification also may be used.

Nucleic acid also may include RNA, or cDNA copied from RNA. In some embodiments, the immobilized nucleic acid may be cDNA, such as in an expression array. cDNA as used herein refers to DNA which is copied from RNA. cDNA copied from mRNA does not include regulatory gene sequences such as are present in genomic DNA.

Methods of purifying genomic DNA and/or RNA from a variety of samples are well-known in the art. An expression array may be prepared by oligo dT priming or random priming with hexomers. The random primer oligos that have 5' ligatable ends. After priming and extension to produce cDNA, the ligatable ends of the cDNA are ligated to a capture sequence via a bridging oligo. cDNA with capture sequences may then be hybridized to a solid phase containing immobilized nucleic acid probe sequences. The capture sequence may be detected with an appropriate labeled reagent (e.g. labeled dendrimeric nucleic acid). Exemplary supplies and protocols for preparing an expression array are available from manufacturers, for example, Genisphere.

A nucleic acid may range in size from about 20 to about 200 nucleotides; about 200 to about 1,000 nucleotides; about 1,000 to about 100,000 nucleotides; or about 100,000 to about 1,000,000 nucleotides in length. Suitable nucleic acids for preparing the substrates described herein are typically at least about 250 nucleotides in length, and more typically at least about 500 nucleotides in length, at least about 1000 nucleotides in length, and/or at least about 5000 nucleotides in length. Nucleic acid of the present method may be contained within a nucleic acid vector (e.g., plasmids, cosmids, etc.), or an artificial chromosome, such as a bacterial artificial chromosome (BAC) or an *E. coli* P1 derived artificial chromosome (PAC) as is known in the art.

The method may be used in comparative genomic hybridization assays, for example, to detect a "chromosomal abnormality." As used herein, "chromosomal abnormality" refers to any difference in the DNA sequence from a wild-type or normal. A chromosomal abnormality may reflect a difference between the full genetic complement of all chromosomes contained in an organism, or any portion thereof, as compared to a normal full genetic complement of all chromosome in that organism. For example, a chromosomal abnormality may include a change in chromosomal copy number (e.g., aneuploidy), or a portion thereof (e.g., deletions, amplifications); or a change in chromosomal structure (e.g., translocations, mutations). "Aneuploid cell" or "aneuploidy" as used herein, refers to a cell having an abnormal number of at least one chromosome in interphase. For example, a normal human cell contains a total of 46 chromosomes in interphase, or 2 copies of each of chromosomes 1 through 22, and 2 sex chromosomes (XX or XY). An abnormal chromosomal copy number is any number other than two of the normal chromosomal complement of two copies of chromosomes 1 through 22, and any combination other than two of the sex chromosomes X and Y.

As used herein, "genetic abnormality" refers to a chromosomal abnormality that is known to be associated with a particular disease condition (e.g., a specific gene mutation causing a dysfunctional protein directly causing a disease state). A chromosomal or genetic abnormality may be hereditary, i.e., passed from generation to generation.

A "sample" as used herein may be acquired from essentially any diseased or healthy organism, including humans, animals and plants, as well as cell cultures, recombinant cells, cell components and environmental sources. Samples may be from any animal, including by way of example and not limitation, humans, dogs, cats, sheep, cattle, and pigs. Samples can be a biological tissue, fluid or specimen. Samples may include, but are not limited to, amniotic fluid, blood, blood cells, cerebrospinal fluid, fine needle biopsy samples, peritoneal fluid, plasma, pleural fluid, saliva, semen, serum, sputum, tissue or tissue homogenates, tissue culture media, urine, and the like. Samples may also be processed, such as sectioning of tissues, fractionation, purification, or cellular organelle separation.

A "test sample" comprises nucleic acids typically from a patient or cell population suspected of, or being screened for, having one or more cell comprising a chromosomal or genetic abnormality. A "reference sample" comprises nucleic acids typically from a normal patient or wild-type cell population with a normal genetic profile.

A "label" or "detectable label" as used herein refers any moiety used to achieve a hybridization signal detectable by spectroscopic, photochemical, biochemical, immunochemical, electromagnetic, radiochemical, or chemical means, such as fluorescence, chemifluoresence, or chemiluminescence, or any other appropriate means. Preferred detectable labels include fluorescent dye molecules, or fluorophores, such as fluorescein, phycoerythrin, Cy3™, Cy5™, allophycocyanine, Texas Red, peridenin chlorophyll, cyanine, FAM, JOE, TAMRA, tandem conjugates such as phycoerythrin-Cy5™, and the like. The detectable label may be linked directly or indirectly to the samples of nucleic acids prior to or after hybridization.

A "linkage" of a detectable label as used herein, means that the label is physically associated with nucleic acids in a sample. In a preferred embodiment, either the first linkage or the second linkage is susceptible to selective removal, i.e., the label is associated in different manner that may be dissociated or cleaved to remove the label from the nucleic acids. Examples of pairs of linkages (i.e., a differential linkage where one linker of the pair is susceptible to selective removal) include linkage via two different chemical linkers, two different oligonucleotides, or two different peptide sequences, wherein the chemical linkers, oligonucleotides or peptide sequences differ in susceptibility to temperature, pH hydrolysis, radiation (e.g., nucleotide stretches or chemical entities sensitive to ultraviolet radiation; e.g., photocleavable entities), oxidative conditions, atmospheric conditions (e.g., exposure to ozone), buffer conditions, hydrolysis by an external agent (e.g., an enzyme, such as a restriction endonuclease or a homing endonuclease), or chemical cleavage (e.g., linkers containing a diol that can be selectively cleaved using saturated aqueous $NaIO_4$ for 30-40 minutes, or linkers containing a disulfide that can be cleaved with dithiothreitol or any other appropriate reducing reagent, such as those available from Fidelity Systems, Inc. Gaithersburg, Md.).

Sources of Nucleic Acids

In one aspect, the present method can be used to detect a chromosomal abnormality in a test sample. In a preferred embodiment, the test sample is obtained from a patient, more preferably, the test sample is suspected of comprising cancerous cells. In another preferred embodiment, the test sample contains cells, tissues or fluid obtained from a patient suspected of having a pathology or a condition associated with a chromosomal or genetic abnormality. The causality, diagnosis or prognosis of the pathology or condition may be associated with genetic defects, e.g., with genomic nucleic acid base substitutions, amplifications, deletions and/or translocations. Samples may include, but are not limited to, amniotic fluid, biopsies, blood, blood cells, bone marrow, cerebrospinal fluid, fecal samples, fine needle biopsy samples, peritoneal fluid, plasma, pleural fluid, saliva, semen, serum, sputum, tears, tissue or tissue homogenates, tissue culture media, urine, and the like. Samples may also be processed, such as sectioning of tissues, fractionation, purification, or cellular organelle separation.

Methods of isolating cell, tissue or fluid samples are well known to those of skill in the art and include, but are not limited to, aspirations, tissue sections, drawing of blood or other fluids, surgical or needle biopsies, and the like. Samples derived from a patient may include frozen sections or paraffin sections taken for histological purposes. The sample can also be derived from supernatants (of cell cultures), lysates of cells, cells from tissue culture in which it may be desirable to detect levels of mosaicisms, including chromosomal abnormalities and copy numbers.

In a preferred embodiment, a sample suspected of containing cancerous cells is obtained from a human patient. Samples can be derived from patients using well-known techniques such as venipuncture, lumbar puncture, fluid sample such as saliva or urine, tissue or needle biopsy, and the like. In a patient suspected of having a tumor containing cancerous cells, a sample may include a biopsy or surgical specimen of the tumor, including for example, a tumor biopsy, a fine needle aspirate, or a section from a resected tumor. A lavage specimen may be prepared from any region of interest with a saline wash, for example, cervix, bronchi, bladder, etc. A patient sample may also include exhaled air samples as taken with a breathalyzer or from a cough or sneeze. A biological sample may also be obtained from a cell or blood bank where tissue and/or blood are stored, or from an in vitro source, such as a culture of cells. Techniques for establishing a culture of cells for use as a sample source are well known to those of skill in the art.

In another aspect, the present method can be used to detect a chromosomal or genetic abnormality in a fetus. Prenatal diagnosis of a fetus may be indicated for women at increased risk of carrying a fetus with chromosomal or genetic abnormalities. Risk factors are well known in the art, and include, for example, advanced maternal age, abnormal maternal serum markers in prenatal screening, chromosomal abnormalities in a previous child, a previous child with physical anomalies and unknown chromosomal status, parental chromosomal abnormality, and recurrent spontaneous abortions.

The present methods can be used to perform prenatal diagnosis using any type of embryonic or fetal cell. Fetal cells can be obtained through the pregnant female, or from a sample of an embryo. Thus, fetal cells are present in amniotic fluid obtained by amniocentesis, chorionic villi aspirated by syringe, percutaneous umbilical blood, a fetal skin biopsy, a blastomere from a four-cell to eight-cell stage embryo (pre-implantation), or a trophectoderm sample from a blastocyst (pre-implantation or by uterine lavage).

The present methods may utilize a first population of nucleic acids obtained from the test sample, and a second population of nucleic acids obtained from a reference sample. The reference sample may be any cells, tissues or fluid as provided herein, obtained from an individual, or any cell culture or tissue culture, that does not contain any genetic abnormality, i.e., that has a normal genetic complement of all chromosomes.

Association of Label with Nucleic Acids

The nucleic acids of a test sample and/or a reference sample typically are associated with a detectable label, either prior to or subsequent to hybridization. In preferred embodiments, the label is detectable by optical means, most preferably a fluorescent label or fluorophore. The detectable label can be incorporated into, associated with or conjugated to a nucleic acid. The association between the nucleic acid and the detectable label can be covalent or non-covalent. According to the present method, detectable labels that are the same or different may be used to label both the nucleic acids of a test sample and/or the nucleic acids of a reference sample. Labels can be attached by spacer arms of various lengths to reduce potential steric hindrance or impact on other useful or desired properties. See, e.g., Mansfield, *Mol. Cell. Probes* 9:145-156, 1995.

Useful labels include, e.g., fluorescent dyes (e.g., Cy5™, Cy3™, FITC, rhodamine, lanthamide phosphors, Texas red), $^{32}$P, $^{35}$S, $^{3}$H, $^{14}$C, $^{125}$I, $^{131}$I, electron-dense reagents (e.g., gold), enzymes, e.g., as commonly used in an ELISA (e.g., horseradish peroxidase, beta-galactosidase, luciferase, alkaline phosphatase), calorimetric labels (e.g., colloidal gold), magnetic labels (e.g., Dynabeads™), biotin, dioxigenin, or haptens and proteins for which antisera or monoclonal antibodies are available. The label can be directly incorporated into the nucleic acid to be detected, or it can be attached to a probe (e.g., an oligonucleotide) or antibody that hybridizes or binds to the nucleic acid to be detected.

In preferred embodiment the detectable label is a fluorophore. The term "fluorophore" as used herein refers to a molecule that absorbs a quantum of electromagnetic radiation at one wavelength, and emits one or more photons at a different, typically longer, wavelength in response. Suitable fluorescent moieties include the following fluorophores known in the art.

Arrays and Nucleic Acid Printing

The methods described herein utilize immobilized nucleic acid. As used herein, "immobilized" or "bound" or means that the nucleic acid is covalently and/or non-covalently coupled (either directly or indirectly) to a substrate, such that the nucleic acid is not substantially removed during a hybridization assay that includes one or more washing steps under high stringency conditions. High stringency conditions are known in the art and may include low salt concentrations (e.g., <4×SSC buffer and/or <2×SSC buffer), the presence of non-ionic detergent (e.g., 0.1% SDS), and/or relatively high temperatures (e.g., >55° C. and/or >70° C.).

The nucleic acids utilized in the disclosed methods can be immobilized to a substrate to prepare an array using any known method for making nucleic acid arrays. Suitable methods that may be used in whole or in part or as variations thereof are disclosed, for example, in U.S. Pat. Nos. 6,562,565; 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston, *Curr. Biol.* 8:R171-R174, 1998; Schummer, *Biotechniques* 23:1087-1092, 1997; Kern, *Biotechniques* 23:120-124, 1997; Solinas-Toldo, *Genes, Chromosomes & Cancer* 20:399-407, 1997; Bowtell, *Nature Genetics Supp.* 21:25-32, 1999. See also published U.S. Patent Applications Nos. 20010018642; 20010019827; 20010016322; 20010014449; 20010014448; 20010012537; 20010008765.

The term "array," "microarray," "biochip," or "chip" as used herein, refers to a plurality of "probe elements," or "printed samples" or "spots", each comprising a defined amount of one or more biological molecules, e.g., polypeptides, nucleic acid molecules, or probes, deposited at discrete locations on a substrate surface. As used herein, the term "nucleic acid array" refers to an array where the elements comprise nucleic acid samples. In preferred embodiments, the plurality of spots comprises nucleic acid samples, deposited at preferably at least about 50, at least about 100, at least about 300, or at least about 500 discrete locations on the surface. The plurality may comprise multiple repeats of the same nucleic acid segments, a variety of different nucleic acid segments, or combinations of the two to produce multiple spots (e.g., duplicate spots, triplicate spots, quadruplicate spots, quintuplicate spots, etc.). In one embodiment, the plurality comprises multiple repeats of the same nucleic acid segments to produce multiple spots.

The term "printing" as used herein, refers to the process of depositing nucleic acid samples onto discrete locations of a solid surface. The term "printing buffer" or "printing solution" as used herein, refers to a solution that is deposited to the array surface. Nucleic acid that is to be printed in an array is contacted with an appropriate printing solution prior to printing the array.

For CGH applications, an array may include a plurality of printed nucleic acid samples that together represents a chromosomal region of interest, a chromosome of interest, or an entire genome of interest. The plurality may reflect only portions of the total sequence. For example, an array of nucleic acid samples together representing a complete chromosome may include segments of 150 kb in length, each segment being the sole sample from every 3-4 MB of chromosomal sequence. In this case, the array can be stated to represent locations that are spaced at intervals about 3-4 megabases (MB) along the chromosome. In such case, arrays with higher resolution can be prepared where each sample of nucleic acid is taken from the target chromosome at intervals of about 2-3 megabases, or more preferably at intervals of about 1-2 megabases. As noted above, arrays may represent all chromosomes of a genome.

Hybridization

The methods used herein related to hybridization (or pre-hybridization) may incorporate all known methods and means (and variations thereof) of hybridization, including those useful for comparative genomic hybridization, see, e.g., U.S. Pat. Nos. 6,197,501; 6,159,685; 5,976,790; 5,965,362; 5,856,097; 5,830,645; 5,721,098; 5,665,549; 5,635,351. See also Diago, *Am. J. Pathol.* 158:1623-1631, 2001; Theillet, *Bull. Cancer* 88:261-268, 2001; Werner, *Pharmacogenomics* 2:25-36, 2001; Jain, *Pharmacogenomics* 1:289-307, 2000.

The term "hybridization" (or prehybridization) as used herein, refers to the pairing of substantially complementary nucleotide sequences (strands of nucleic acid) to form a duplex or heteroduplex through formation of hydrogen bonds between complementary base pairs in accordance with Watson-Crick base pairing. Hybridization is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved (e.g., temperature and salt concentration), and the $T_m$ of the formed hybrid.

Generally, nucleic acid hybridizations comprise the following major steps: (1) immobilization of nucleic acids to a support to provide an immobilized probe; (2) pre-hybridization treatment to increase accessibility of the probe and to reduce nonspecific binding; (3) hybridization of a mixture of target nucleic acids to the probe; (4) post-hybridization washes to remove nucleic acid fragments not hybridized to the probe; and (5) detection of the target nucleic acid hybridized to the probe. The reagent used in each of these steps and their conditions for use may vary depending on the particular application. As used herein, the terms "probe" and "target" may be used interchangeably. For example, the support may include an immobilized "target" nucleic acid to which a mixture of "probe" nucleic acids are hybridized.

The nucleic acid that is immobilized (e.g., as a probe) on a solid support or substrate as described herein remains substantially immobilized during standard hybridization steps, including high stringency wash conditions. For example, the nucleic acid remains substantially immobilized during washing conditions with 2% SSC buffer, 0.1% SDS, at temperatures of about 55° C. or greater (and more suitably at temperatures of about 70° C. or greater).

Hybridization conditions may be high, moderate or low stringency conditions. Ideally, nucleic acids will hybridize only to complementary nucleic acids and will not hybridize to other non-complementary nucleic acids in the sample. The hybridization conditions can be varied to alter the degree of stringency in the hybridization and reduce background signals as is known in the art. For example, if the hybridization conditions are high stringency conditions, a nucleic acid will bind only to nucleic acid target sequences with a very high degree of complementarity. Low stringency hybridization conditions will allow for hybridization of sequences with some degree of sequence divergence. The hybridization conditions will vary depending on the biological sample, and the type and sequence of nucleic acids. One skilled in the art will know how to optimize the hybridization conditions to practice the present method.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have a high frequency of complementary base sequences.

Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5×Denhardt's solution, 5×SSC (saline sodium citrate) 0.2% SDS (sodium dodecyl sulphate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2× SSC, 0.2% SDS, at 65° C. Low stringency refers to conditions equivalent to hybridization in 10% formamide, 5×Denhardt's solution, 6×SSC, 0.2% SDS, followed by washing in 1×SSC, 0.2% SDS, at 50° C.

As used herein, the terms "complementary" or "complementarity" are used in reference to polynucleotides (i.e., a sequence of nucleotides such as an oligonucleotide or a target nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association". For example, for the sequence "5'-A-G-T-3'" is complementary to the sequence "3'-T-C-A-5'". Certain bases not commonly found in natural nucleic acids may be included in the nucleic acids of the present method and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Complementarity may be "partial" in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand. As used herein, "non-specific nucleic acid" means that the nucleic acid lacks substantial complementarity with another nucleic acid (e.g., a target or a probe).

The term "homology" and "homologous" refers to a degree of identity. There may be partial homology or complete homology. A partially homologous sequence is one that is less than 100% identical to another sequence. Preferably, homologous sequences have an overall identity of at least 70% or at least 75%, more preferably at least 80% or at least 85%, most preferably at least 90% or at least 95%.

As used herein, the term "$T_m$" is used in reference to the "melting temperature". The melting temperature is the temperature at which a sample of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41$ (% G+C), when a nucleic acid is in aqueous solution at 1 M NaCl (see, e.g., Anderson and Young, Quantitative Filter Hybridization, in Nucleic Acid Hybridization, 1985). Other references (e.g., Allawi and SantaLucia, *Biochemistry* 36:10581-94, 1997) include more sophisticated computations which take structural and environmental, as well as sequence characteristics into account for the calculation of $T_m$.

Blocking Repetitive Nucleic Acids from Hybridizing

In many genomes, including the human genome, a major portion of shared repetitive DNA is contained within a few families of highly repeated sequences such as Alu. In some applications it is necessary to block the hybridization capacity of these types of repetitive nucleic acid sequences. A number of methods for removing and/or disabling the hybridization capacity of repetitive sequences are known (see, e.g., WO 93/18186).

For example, bulk procedures may be used to remove repetitive nucleic acid sequences. Bulk procedure methods exploit the fact that the hybridization rate of complementary sequences increases as their concentration increases. Thus, repetitive sequences, which are generally present at high concentration will become double stranded more rapidly than other sequence after denaturation and incubation under hybridization conditions. The double stranded nucleic acids are then removed and the remainder used in hybridizations. Methods of separating single from double stranded sequences include using hydroxyapatite or immobilized complementary nucleic acids attached to a solid support, and the like. Alternatively, the partially hybridized mixture can be used and the double stranded sequences will be unable to hybridize to the target.

Alternatively, unlabeled sequences which are complementary to the sequences whose hybridization capacity is to be inhibited can be added to the hybridization mixture. This method can be used to inhibit hybridization of repetitive sequences as well as other sequences. For example, Cot-1 DNA can be used to selectively inhibit hybridization of repetitive sequences in a sample. To prepare Cot-1 DNA, DNA is extracted, sheared, denatured and re-natured. Because highly repetitive sequences re-anneal more quickly, the resulting hybrids are highly enriched for these sequences. Cot-1 DNA is genomic DNA enriched in repetitive sequences. The remaining single stranded (i.e., single copy sequences) is digested with S1 nuclease and the double stranded Cot-1 DNA is purified and used to block hybridization of repetitive sequences in a sample. Although Cot-1 DNA can be prepared as described above, it is also commercially available (BRL). Typically, Cot-1 DNA is added at a concentration of about 0.2, mg/ml, 0.5 mg/ml, 0.7 mg/ml, 1 mg/ml, 1.2 mg/ml, 1.5 mg/ml, 1.7 mg/ml, or about 2 mg/ml. in a preferred embodiment, Cot-1 DNA is used at concentrations higher than about 1 mg/ml to block hybridization of repetitive sequences such as during prehybridization or during hybridization.

Acoustic Wave Technology

The method disclosed herein relates to applying acoustic surface waves to one or more nucleic acids during a nucleic acid hybridization assay. In the case of prehybridization, acoustic waves can be applied to the non-specific nucleic acid while in contact with the solid phase containing immobilized nucleic acid probes. Similarly, in hybridization, acoustic waves can be applied to the nucleic acid target molecules while in contact with the solid phase containing immobilized nucleic acid probes. In addition, acoustic waves may be applied to wash solutions while in contact with the solid phase to facilitate removal of non-hybridized or weakly hybridized nucleic acid (i.e., to facilitate washing).

A wide variety of acoustic wave technology may be suitable for the present method. In particular, the technology described in U.S. Pat. No. 6,777,245 may be suitable for the present method. One suitable instrument for generating surface acoustic waves to facilitate hybridization is the SlideBooster SB400/SB800 (Advalytix AG).

Interpretation of Array-based CGH

In the disclosed method, the copy number of particular nucleic acid sequences in a test sample and/or a reference sample may be compared by hybridizing the samples to one or more target nucleic acid segments. The hybridization signal intensity, and the ratio of intensities, produced by the detectable label associated with a sample may then be determined. Typically, the greater the ratio of the signal intensities on a target nucleic acid segment, the greater the copy number ratio of sequences in the samples that bind to that element. Thus comparison of the signal intensity ratios among target nucleic acid segments permits comparison of copy number ratios of different sequences in the genomic nucleic acids of test samples.

Detectable labels may be detected by using any suitable apparatus and method in the art, including any apparatus or methods to detect detectable labels associated with multiple nucleic acids of a sample, an individual member of the nucleic acids of a sample, or an array-immobilized nucleic acid segment, or, any apparatus or methods to detect nucleic acids specifically hybridized to each other. Devices and methods for the detection of fluorophores, including multiple fluorophores, are well known in the art, see, e.g., U.S. Pat. Nos. 5,539,517; 6,049,380; 6,054,279; 6,055,325; and 6,294,331. Any known device or method, or variation thereof, can be used or adapted to practice the present method, including array reading or "scanning" devices, such as scanning and analyzing multicolor fluorescence images; see, e.g., U.S. Pat. Nos. 6,294,331; 6,261,776; 6,252,664; 6,191,425; 6,143,495; 6,140,044; 6,066,459; 5,943,129; 5,922,617; 5,880,473; 5,846,708; 5,790,727; and, the patents cited in the discussion of arrays, herein. See also published U.S. patent application Ser. Nos. 20010018514; 20010007747; and published international patent applications Nos. WO0146467 A; WO9960163 A; WO0009650 A; WO0026412 A; WO0042222 A; WO0047600 A; and WO0101144 A.

For example a spectrograph can image an emission spectrum onto a two-dimensional array of light detectors; a full spectrally resolved image of the array is thus obtained. Photophysics of the fluorophore, e.g., fluorescence quantum yield and photodestruction yield, and the sensitivity of the detector are read time parameters for an oligonucleotide array. With sufficient laser power and use of Cy5™ or Cy3™, which have lower photodestruction yields an array can be read in less than 5 seconds.

Charge-coupled devices, or CCDs, are used in microarray scanning systems, including practicing the present method. Color discrimination can also be based on 3-color CCD video images; these can be performed by measuring hue values. Hue values are introduced to specify colors numerically. Calculation is based on intensities of red, green and blue light (RGB) as recorded by the separate channels of the camera. The formulation used for transforming the RGB values into hue, however, simplifies the data and does not make reference to the true physical properties of light. Alternatively, spectral imaging can be used; it analyzes light as the intensity per wavelength, which is the only quantity by which to describe the color of light correctly. In addition, spectral imaging can provide spatial data, because it contains spectral information for every pixel in the image. Alternatively, a spectral image can be made using brightfield microscopy, see, e.g., U.S. Pat. No. 6,294,331.

EXAMPLE

Rapid Hybridization of BAC Arrays

Array Blocking

Cot-1 DNA (30 µg) was precipitated with salmon sperm testicle DNA (15 µg) by adding 1/12 volume of 5 M NaCl and 75% isopropanol by volume. The mixture was allowed to incubate at room temperature of 20 minutes and then centrifuged for 20 minutes to collect the precipitated pellet. The pellet was washed with 400 µl 70% EtOH.

The pellet was then dissolved in 10 µl sterile water and 30 µl hybridization buffer and placed on the array. Dynamic hybridization was allowed to proceed at 37° C. for 2 hours on a Slide Booster hybridization station (Advalytix AG).

Advantageously, the acoustic surfaces are generated by electric stimulation. A simple possibility for this is offered by interdigital converters, so-called interdigital transducers. In the simplest embodiment, these consist of at least two metal structures the mesh in the manner of combs, applied in at least one planar-technology process to a substrate surface. If a high-frequency alternating-voltage signal is applied to such an interdigital structure, then a crystal deformation results according to the inverse piezoelectric effect, which has the spatial periodicity of the interdigital converter and the time periodicity of the high-frequency alternating voltage. To the extent that the applied high-frequency alternating-voltage signal is applied in resonance with the speed of sound on the surface involved, then an acoustic surface wave spreads out perpendicularly to the axis of the converter. The corresponding resonance condition is f=v/λ, where f is the frequency of the applied alternating field, v is the speed of sound of the surface waves, and λ is the spatial periodicity of the interdigital converter.

In the process according to the invention, surface waves are generated with the aid of at least one surface-wave generating device, the impulse of which is made to interact with at least one quantity of matter, in order to cause movement in a desired direction. The device according to the invention also has at least one device for generating surface waves on a solid-body surface in at least one direction of spreading and an interaction region, in which the quantity of matter can interact with the at least one surface wave, in order to cause movement of the quantity of matter through an impulse transfer by the surface wave or surface waves.

The array was then washed either manually or by utilizing an Automatic Rapid Wash Station.

DNA Labeling and Hybridization

A sample including 2 μg of test DNA and 2 μg of reference DNA in 55 μl sterile ddH$_2$O was sonicated. The sonicated sample (5 μl) was subjected to electrophoresis on a 1% agarose gel to verify that the sample was fragmented (i.e., into 500-5000 bp fragments).

Fractions of the sample (25 μl) were divided into two tubes for separate labeling with Cy5 and Cy3.

Random primers (20 μl) were added to each tube. Add 20 μl of Random Primers to each tube. The tube contents was heated at 100° C. for 5 minutes and snap cooled on an ice slurry for 5 minutes to denature the DNA in the samples.

A Master Labeling Mix (5 μl) containing 5 μl of dNTP mix, 3 μl of fluorescent dye (Cy5 or Cy3), and 2 μl of klenow enzyme was added to each tube. The contents of the tube were fragmented and then incubated for 2 hours in a water bath at 37° C. The labeled sample (5 μl) was subjected to electrophoresis on a 1% agarose gel to confirm the presences of labeled fragments in the 100-500 bp range. To stop the reaction, 0.5 M EDTA (5 μl) was added to the labeled samples and the samples were heated for 10 minutes at 72° C. The labeled samples were purified using a QIAquick PCR purification kit.

Cot-1 DNA (50 μg) was added to each of the Cy5 and Cy3 labeled samples. The DNA in the samples was then precipitated by adding 1/12 volume of 5 M NaCl and 75% isopropanol by volume. The mixtures were allowed to incubate at room temperature for 20 minutes and the precipitated DNA was collected as a pellet by centrifuging for 20 minutes in a microcentrifuge at 13000 r.p.m. The pellets were rinsed with 700 μl of 70% ethanol.

The pellets were then dissolved in 101 of sterile ddH$_2$O and 30 ml of hybridization buffer. The DNA was denatured by heating the tubes at 72° C. for 10 minutes and then snap-cooled on an ice slurry for 5 minutes.

Next, the tubes were incubated at 37° C. for 30 minutes. The DNA was then added to the blocked array positions on a slide placed in an Advalytics Hybridization Station (Advalytix AG). Dynamic hybridization was allowed to occur for 3 hours (3-hour hybridization). The slides were then washed either manually or utilizing an automated rapid Advalytics wash station.

The slides were scanned with an Axon scanner and the data was analyzed in comparison to an overnight manual hybridization (16-hour hybridization). Image intensities derived from the 3-hour hybridization and 16-hour hybridization were equivalent.

All references, patents, and/or applications cited in the specification are indicative of the level of skill of those skilled in the art to which the invention pertains, and are incorporated by reference in their entireties, including any tables and figures, to the same extent as if each reference had been incorporated by reference in its entirety individually.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

As used herein, the term "about" means "approximately" or "nearly." In the context of numerical values, the term may be construed to estimate a value that is ±10% of the value or range recited.

What is claimed is:

1. A method for performing comparative genomic hybridization to immobilized nucleic acid, comprising the following steps:
   a) performing a prehybridization step comprising contacting a solid support comprising one or more immobilized nucleic acid probe molecules under hybridization conditions with a non-specific blocking nucleic acid at a concentration of at least 0.9 mg/ml, said one or more immobilized nucleic acid probe molecules capable of hybridizing with a sequence complementary thereto;
   b) hybridizing a test sample containing genomic nucleic acid target molecules comprising a first detectable fluorescent label and a reference sample containing genomic nucleic acid reference molecules comprising a second detectable fluorescent label to the solid support under hybridizing conditions;
   c) applying acoustic surface waves during step a) and step b), wherein the acoustic surface waves are generated by an alternating-voltage electrical signal, such that the acoustic surface waves cause movement of the test sample and the reference sample through impulse transfer;
   d) washing the solid support following step a), step b), or both step a) and b);
   e) determining the relative hybridization of the test sample and the reference sample to one or more nucleic acid probes of the solid support by detecting the fluorescence from the detectable labels on the target nucleic acid molecules and the reference nucleic acid molecules, wherein the relative hybridization indicates the comparative hybridization of the test and reference samples.

2. The method of claim 1 wherein said washing further includes application of acoustic surface waves to the washing step.

3. The method of claim 1 wherein hybridization in step b) further comprises addition of a non-specific blocking nucleic acid.

4. The method of claim 3 wherein said non-specific blocking nucleic acid is added at a concentration of at least 0.9 mg/ml.

5. The method of claim 4, wherein the non-specific blocking nucleic acid comprises Cot-1 DNA.

6. The method of claim 1, wherein step a) and b) are performed for less than 3 hours.

7. The method of claim 1, wherein said washing is performed for less than 1 hour.

8. The method of claim 1, wherein step a) or b) is performed for less than 1 hour.

9. The method of claim 1, wherein the method is performed in less than 5 hours.

10. The method of claim 1, wherein the method is performed in less than 8 hours.

11. The method of claim 1, wherein the one or more nucleic acid probes comprises one or more bacterial artificial chromosomes.

12. The method of claim 1, wherein the non-specific blocking nucleic acid comprises Cot-1 DNA.

\* \* \* \* \*